United States Patent [19]

Aotani et al.

[11] Patent Number: 5,202,216

[45] Date of Patent: Apr. 13, 1993

[54] POSITIVE WORKING PHOTOSENSITIVE COMPOSITION

[75] Inventors: Yoshimasa Aotani; Akira Umehara, both of Shizuoka; Tsuguo Yamaoka, Funabashi, all of Japan

[73] Assignee: Fuji Photo Film Co., Ltd., Minami-Ashigara, Japan

[21] Appl. No.: 608,801

[22] Filed: Nov. 5, 1990

[30] Foreign Application Priority Data

Nov. 13, 1989 [JP] Japan .................................. 1-294422

[51] Int. Cl.$^5$ ........................... G03C 1/56; G03C 1/72
[52] U.S. Cl. ..................................... 430/176; 430/192; 430/270; 430/326
[58] Field of Search ................ 430/270, 192, 176, 326; 522/31, 15

[56] References Cited

U.S. PATENT DOCUMENTS

| | | | |
|---|---|---|---|
| 3,269,837 | 8/1966 | Süs | 430/192 |
| 4,708,925 | 11/1987 | Newman | 430/270 |
| 4,752,552 | 6/1988 | Aoai | |
| 4,786,577 | 11/1988 | Aoai et al. | |
| 4,820,607 | 4/1989 | Aoai | |
| 4,837,124 | 6/1989 | Wu et al. | 522/31 |
| 4,912,018 | 3/1990 | Osuch et al. | 430/270 |
| 4,925,340 | 1/1991 | Palazzotto et al. | 430/270 |
| 4,954,416 | 9/1991 | Wright et al. | 522/15 |

OTHER PUBLICATIONS

"Ammonium", Hackh's Chemical Dictionary, McGraw-Hill Book Co., NY, J. Grant editor, p. 37, 1972.

Primary Examiner—Marion E. McCamish
Assistant Examiner—Christopher D. RoDee
Attorney, Agent, or Firm—Alexandria, VA 22313-1404; Burns, Doane, Swecker & Mathis

[57] ABSTRACT

A positive working photosensitive composition comprising a polymeric compound insoluble in water but soluble in an aqueous alkaline solution and an aromatic sulfonic acid salt of an onium compound. The positive working photosensitive composition having high sensitivity and being capable of forming high-contrast images.

17 Claims, No Drawings

POSITIVE WORKING PHOTOSENSITIVE COMPOSITION

BACKGROUND OF THE INVENTION

1. Field of the Invention

The present invention relates to a photosensitive composition suitable for production of lithographic printing plates and photoresists. More particularly, the present invention relates to a positive working photosensitive composition having high sensitivity and being capable of forming high-contrast images.

2. Description of the Prior Art

In general, the compositions comprising alkali-soluble resins and naphthoquinone diazide compounds as a photosensitive material have been used as a positive working photosensitive composition.

However, there have recently been filed a variety of patent applications relating to positive working photosensitive compositions using photosensitive materials other than naphthoquinone diazide compounds.

For example, U.S. Pat. No. 3,984,253 describes that polyphthalaldehyde is made sensitive to ultraviolet rays, electron beams and X-rays by adding acid-forming compounds such as a diazonium salt to a photosensitive composition in order to form positive images.

Further, U.S. Pat. No. 4,311,782 describes a radiation sensitive mixture to be used for forming positive relief images, which comprises an acid-forming compound and a polymerizable compound having orthocarboxylate units which exist periodically in the molecule of the compound.

Furthermore, Japanese Patent Unexamined Published Application (hereinafter referred to as "J. P. KOKAI") No. 59-45439 describes a resist composition comprising a polymer being unstable to acid and having branched groups and a photopolymerizable initiator capable of forming an acid upon exposure to radiation.

In addition, SPIE vol. 920 Advances in Resist Technology and Processing V (1988), page 33 describes a two-component system positive working photosensitive composition which comprises a metal halide of a triphenylphosphonium or diphenyliodonium compound.

With respect to a method for making a sensitive wavelength higher, J. P. KOKAI No. 59-45439 describes on page 2 that positive working photosensitive compositions are made sensitive to a various wavelength ranging from far ultraviolet rays to visible rays and that, in particular, it is possible to form a resist pattern in the wider area of wavelength ranging from ultraviolet rays to visible rays in case of employing a diaryliodonium salt or a triarylphosphonium salt. Further, U.S. Pat. No. 4,760,013 describes that the sensitive wavelength is made higher by varying the structure of onium compounds.

However, any of the foregoing prior art does not disclose photosensitive compositions having a high sensitivity and having photosensitivity to a wide wavelength area.

SUMMARY OF THE INVENTION

Accordingly, an object of the invention is to provide a positive working photosensitive composition which has high sensitivity and is capable of formimg high-contrast images and which is sensitive to a wide area of wavelength, i.e. sensitive to ultraviolet rays, visible rays, electron beams and X-rays.

According to the present invention, there is provided a positive working photosensitive composition comprising a polymeric compound insoluble in water but soluble in an aqueous alkaline solution and an aromatic sulfonic acid salt of an onium compound.

The inventors of the present invention have found that the spectral sensitivity of the positive working photosensitive composition can be widen to the absorption wavelength area of aromatic sulfonic acid by employing the specific aromatic sulfonic acid according to the present invention as a counter anion for an onium compound. The present invention has been completed based on such a finding.

According to the present invention, there is provided a positive working photosensitive composition sensitive to ultraviolet rays, visible rays, electron beams and X-rays. Namely, the positive working photosensitive composition of the present invention can act as a material for forming positive working images by using the composition comprising a combination of a polymeric compound insoluble in water but soluble in an aqueous alkaline solution and an aromatic sulfonic acid salt of an onium compound such as diaryliodonium or triarylsulfonium and by appropriately selecting a developer. The composition comprising a polymeric compound insoluble in water but soluble in an aqueous alkaline solution and an aromatic sulfonic acid salt of an onium compound is coated, as a thin film, on the substrate, baked under a controlled condition and then imagewise exposed to radiation. The exposed plate thus obtained is optionally subjected to post-baking under a controlled condition and then the exposed portions are selectively removed by the treatment with an alkali developer to thereby obtain positive images.

DETAILED DESCRIPTION OF THE INVENTION

The polymeric compounds insoluble in water but soluble in an alkaline aqueous solution used in the present invention include novolak phenolic resins. Examples of such polymeric compounds are a condensate of formaldehyde with a phenol derivative such as phenol, o-cresol, m-cresol, p-cresol, 2,5-xylenol, 3,5-xylenol and/or t-butylphenol; polyvinylphenol; a hydroxyphenylmethacrylamide copolymer as described in J.P. KOKAI No. 51-36129; and a sunfonamide group- containing polymeric compound as described in European Patent No. 330239. However, the present invention is not restricted to those specific examples.

The amount of the polymeric compound insoluble in water but soluble in an aqueous alkaline solution is about 20–95% by weight, preferably 50–85% by weight based on the total weight of the photosensitive composition (not inclusive of a coating solvent).

The aromatic sulfonic acid salts of the onium compounds used in the present invention as a photosensitive material are represented by the following general formula (1) or (2).

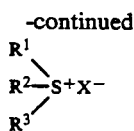

In the foregoing formulas (1) and (2), $Ar^1$ and $Ar^2$ may be the same or different and represent substituted or unsubstituted aromatic groups. The preferred substituents thereof are an alkyl group, a haloalkyl group, a cycloalkyl group, an aryl group, an alkoxy group, a nitro group, a carbonyl group, an alkoxycarbonyl group, a hydroxy group, a mercapto group and a halogen atom, and more preferred are an alkyl group having 1-8 carbon atoms, an alkoxy group having 1-8 carbon atoms, a nitro group and a chlorine atom. $R^1$, $R^2$ and $R^3$ may be the same or different and each represents a substituted or unsubstituted alkyl group or a substituted or unsubstituted aromatic group, preferably an aryl group having 6-14 carbon atoms and an alkyl group having 1-8 carbon atoms or a substituted derivative thereof. The preferred substituents for the aryl group are an alkoxy group having 1-8 carbon atoms, an alkyl group having 1-8 carbon atoms, a nitro group, an oxo group, a hydroxy group and a halogen atom. The preferred substituents for the alkyl group are an alkoxy group having 1-8 carbon atoms, an oxo group and an alkoxycarbonyl group. The two of $R^1$, $R^2$ and $R^3$, or $Ar^1$ and $Ar^2$ may bond together through a single bond or a substituent.

$X^-$ represents an aromatic sulfonic acid anion. The examples are anions of condensed polycyclic aromatic sulfonic acid such as naphthalene-1-sulfonic acid, naphthalene-2-sulfonic acid, anthracene-1-sulfonic acid, 9-nitroanthracene-1-sulfonic acid, 9,10-dichloroanthracene-2-sulfonic acid, 9,10-dimethoxyanthracene-2-sulfonic acid, 9,10-diethoxyanthracene-2-sulfonic acid, anthracene-2-sulfonic acid, phenanthrene-2-sulfonic acid, 9-bromophenanthrene-3-sulfonic acid, 1-methyl-7-isopropylphenanthrene-3-sulfonic acid, pyrene-2-sulfonic acid, benz[a]anthracene-4-sulfonic acid, triphenylene-2-sulfonic acid, chrysene-6-sulfonic acid, 5,6-dichloroanthracene-3-sulfonic acid, 6-nitroacenaphthene-5-sulfonic acid and 2-t-butylnaphthalene-7-sulfonic acid; anions of anthraquinonesulfonic acids and phenanthraquinonesulfonic acids such as 9,10-dioxo-9,10-dihydroanthracene-2-sulfonic acid, 1-bromo-9,10-dioxo-9,10-dihydroanthracene-2-sulfonic acid, 2-chloro-9,10-dioxo-9,10-dihydroanthracene-2-sulfonic acid and 9,10-dioxo-9,10-dihydrophenanthrene-3-sulfonic acid; naphthoquinonesulfonic acid anions such as 1,2-naphthoquinone-4-sulfonic acid, 1,2-naphthoquinonediazide-4-sulfonic acid, 1,2-naphthoquinonediazide-5-sulfonic acid; 2-hydroxy-4-methoxybenzophenone-5-sulfonic acid; and sulfonic acid group-containing dyes such as Phenol Red, Methyl Orange, alizarin S, indigo carmine, Patent Blue, Chlorphenol Red and Chrysophenine. However, the present invention is not restricted to these specific examples.

The examples of the compounds of the general formula (1) used in the present invention are shown below. However, the present invention is not restricted to these specific examples.

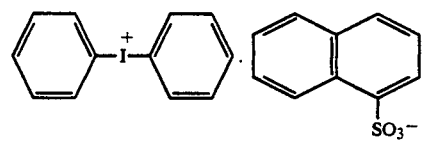

(1-1)

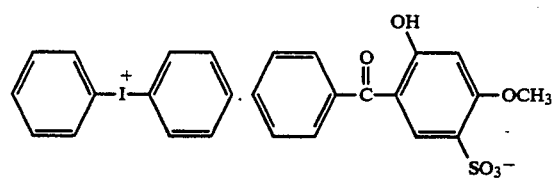

(1-2)

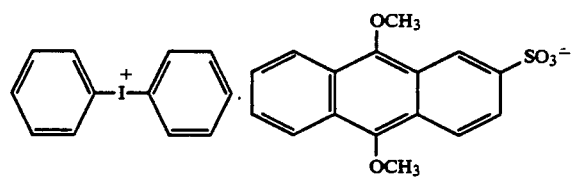

(1-3)

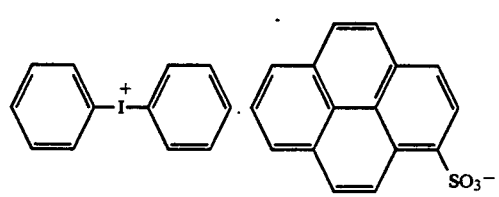

(1-4)

-continued
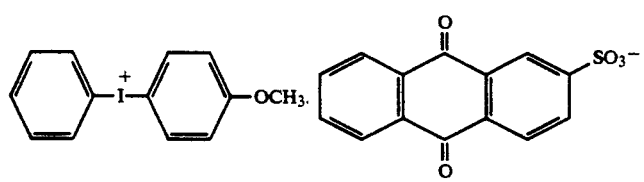 (1-5)
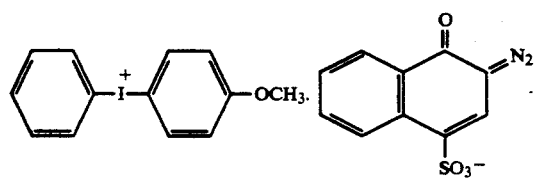 (1-6)
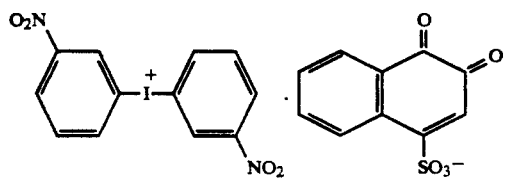 (1-7)
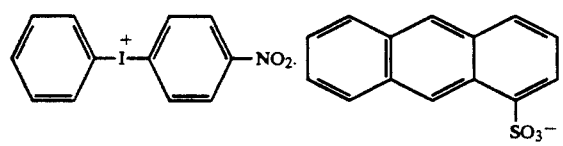 (1-8)
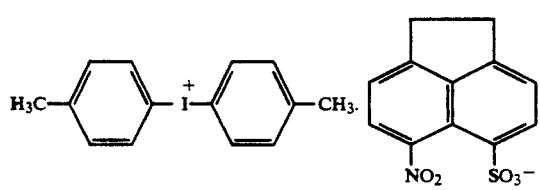 (1-9)
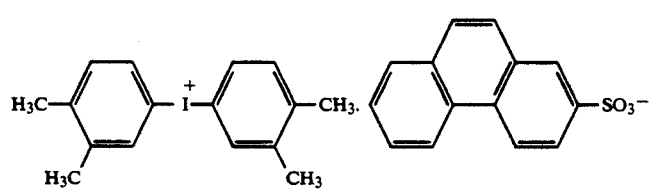 (1-10)
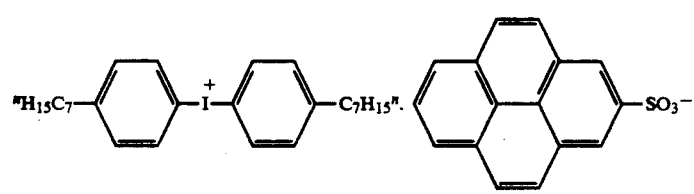 (1-11)
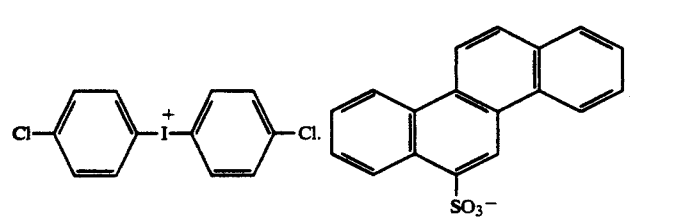 (1-12)

-continued
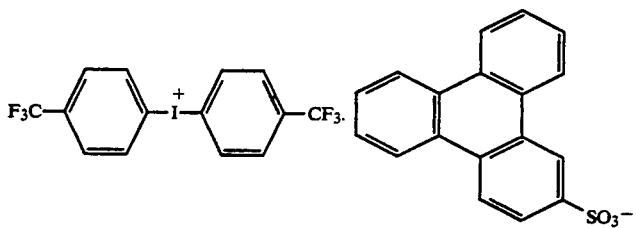 (1-13)
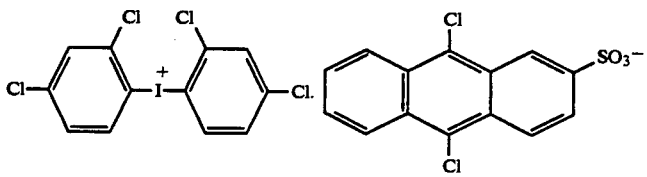 (1-14)
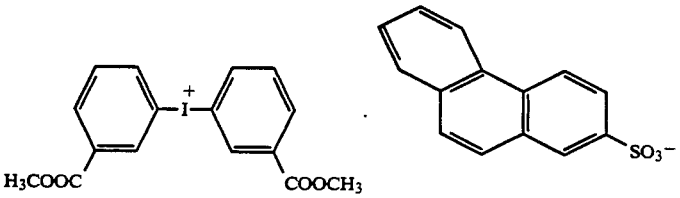 (1-15)
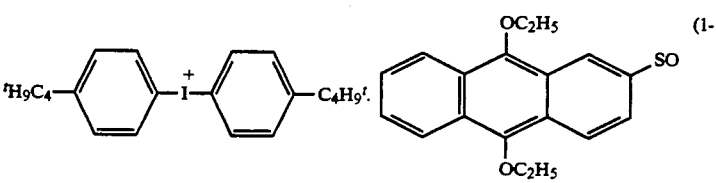 (1-16)
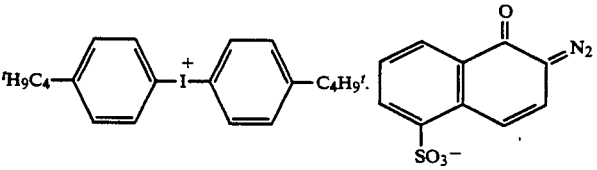 (1-17)
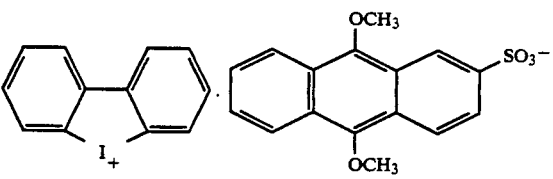 (1-18)
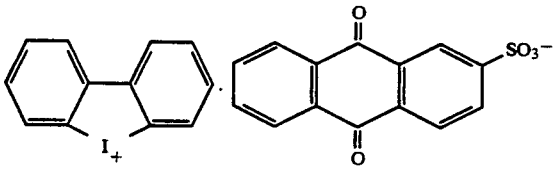 (1-19)
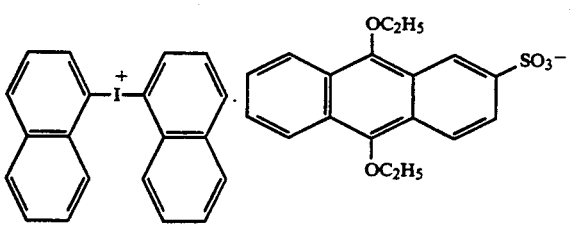 (1-20)
The examples of the compounds of the general formula (2) used in the present invention are shown below. However, the present invention is not restricted to these specific examples.

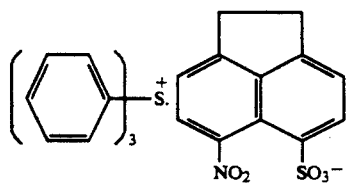 (2-1)
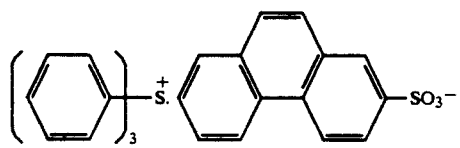 (2-2)
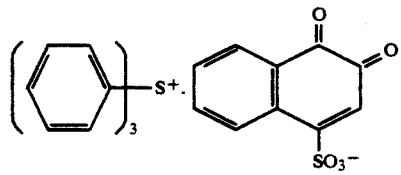 (2-3)
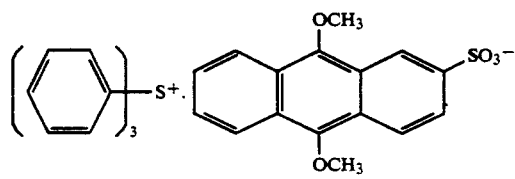 (2-4)
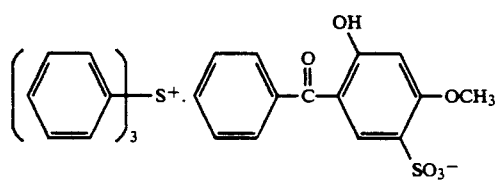 (2-5)
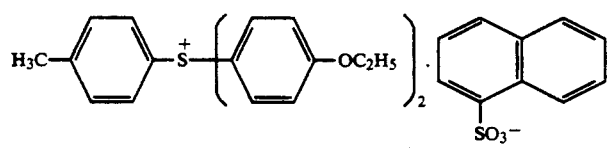 (2-6)
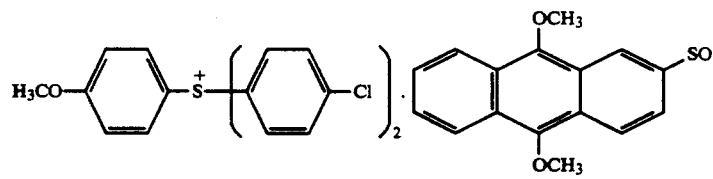 (2-7)
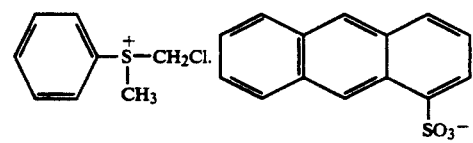 (2-8)
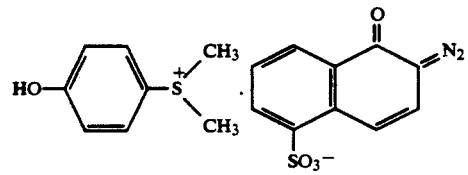 (2-9)

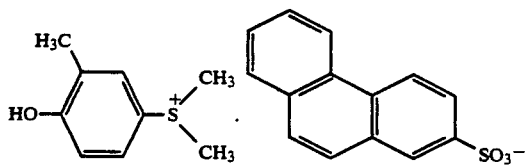 (2-10)
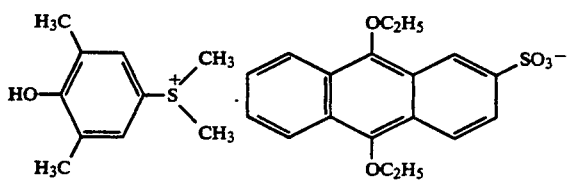 (2-11)
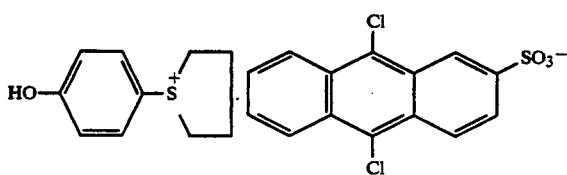 (2-12)
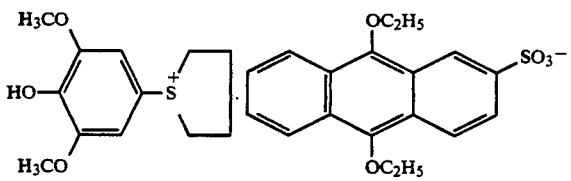 (2-13)
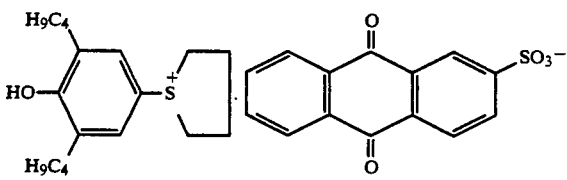 (2-14)
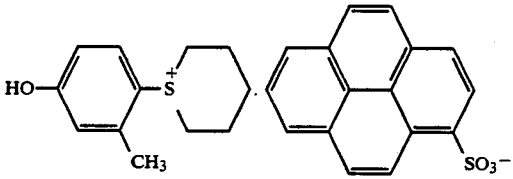 (2-15)
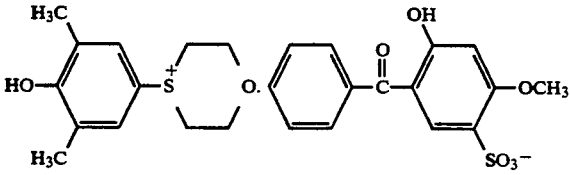 (2-16)
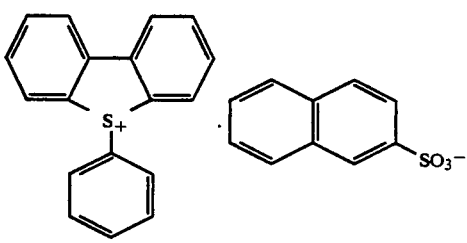 (2-17)

-continued
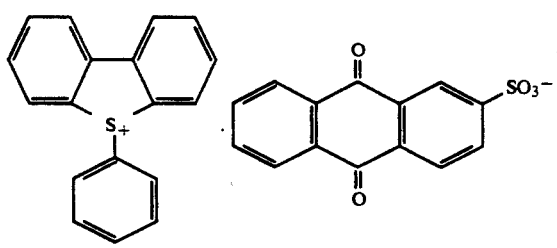 (2-18)
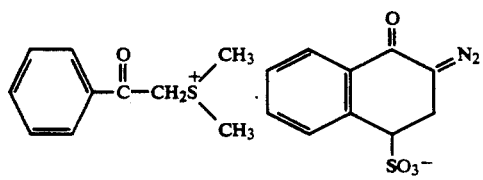 (2-19)
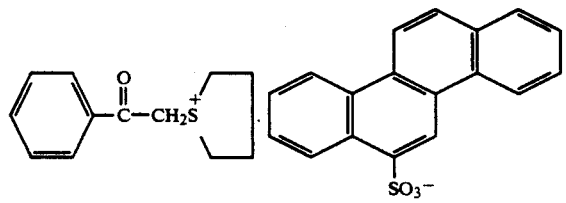 (2-20)
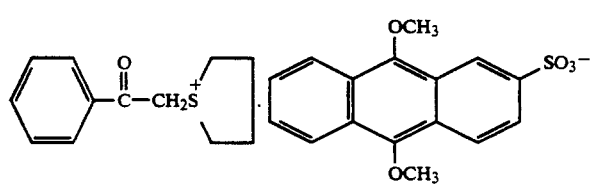 (2-21)
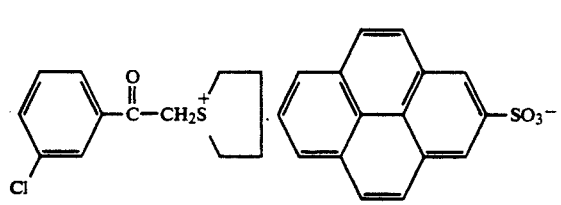 (2-22)
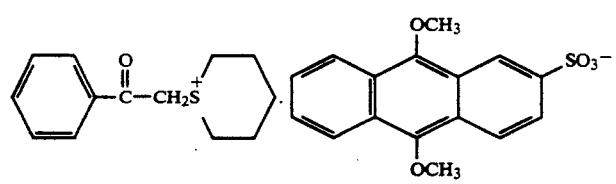 (2-23)
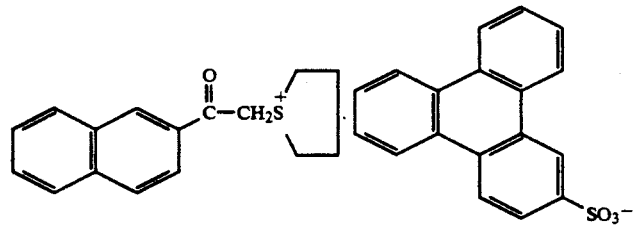 (2-24)
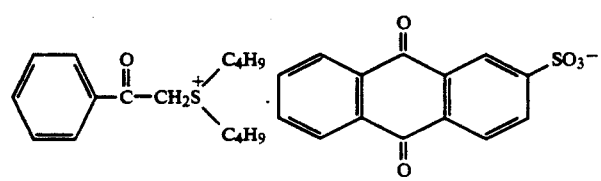 (2-25)

-continued

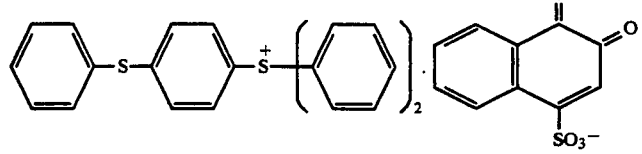
(2-26)

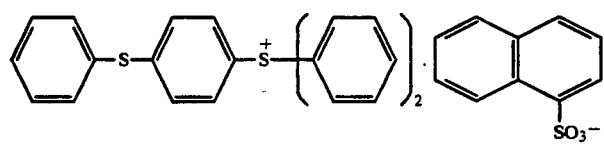
(2-27)

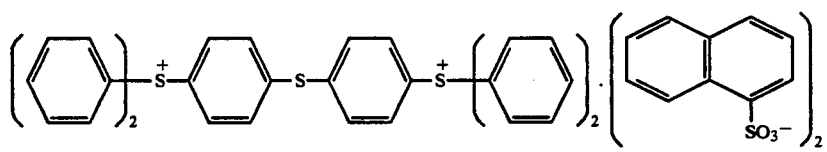
(2-28)

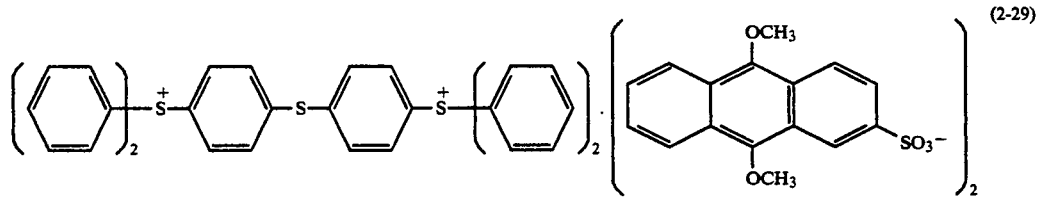
(2-29)

The amount of the aromatic sulfonic acid salt of the onium compound used in the present invention is about 2–60% by weight, more preferably 5–40% by weight based on the total weight of the photosensitive compound (not inclusive of a coating solvent).

The compounds of the general formula (1) or (2) can be obtained by adding an aqueous solution or an alcoholic solution of an aromatic sulfonic acid or sodium salt threreof, to an aqueous solution or an alcoholic solution of halide, bisulfate or perchlorate of the onium compound and then collecting the precipitate thus formed. The methods for producing these onium compounds are disclosed, for example, in "J. Am. Chem. Soc." by J. W. Knapczyk et al., Vol. 91, page 145 (1969), "J. Org. Chem." by A. L. Maycock et al., Vol. 35, page 2532 (1970), "Bull. Soc. Chem. Belg." by E. Goethals et al., Vol. 73, page 546 (1964), "J. Am. Chem. Soc." by H. M. Leicester, Vol. 51, page 3587 (1929), "J. Polym. Soc. Polym. Chem. Ed." by J. V. Crivello et al., Vol. 18, page 2677 (1980), U.S. Pat. Nos. 2,807,648 and 4,247,473, "J. Am. Chem. Soc." by F. M. Beringer et al., Vol. 75, page 2705 (1953) and J. P. KOKAI No. 53-101331.

The photosensitive composition of the present invention may optionally contain dyes, pigments, plasticizers, surfactants, sensitizers and silyl ether compounds as described in J. P. KOKAI No. 61-166543.

Preferred dyes are oil-soluble dyes and basic dyes. Examples of them include Oil Yellow #101, Oil Yellow #130, Oil Pink #312, Oil Green BG, Oil Blue BOS, Oil Blue #603, Oil Black BY, Oil Black BS and Oil Black T-505 (products of Orient Kagaku Kogyo Co.), Crystal Violet (CI 42555), Methyl Violet (CI 42535), Rhodamine B (CI 45170B), Malachite Green (CI 42000) and Methylene Blue (CI 52015).

The photosensitive composition of the present invention is dissolved in a solvent in which all the components are soluble and the solution is applied to a substrate. The preferred solvents are, for example, ethylene dichloride, cyclohexanone, cyclopentanone, γ-butyrolactone, methyl ethyl ketone, ethylene glycol monomethyl ether, ethylene glycol monoethyl ether, 2-methoxyethyl acetate, ethylene glycol monoethyl ether acetate, toluene, ethyl acetate, methyl lactate, ethyl lactate, N,N-dimethylformamide and dimethyl sulfoxide. These solvents are used alone or in combination. The above solvents can also contain surfactants.

The amount of the composition to be applied varies depending on the use. For example, when it is used for the production of a photosensitive lithographic plate, the amount thereof is preferably 0.5 to 4.0 g/m$^2$ (in terms of solid). On the other hand, when it is used for the production of a photoresist, the amount thereof is preferably 0.3 to 2.0 g/m$^2$. As the amount of the applied composition is reduced, the photosensitivity is increased, but the properties of the photosensitive film become poor.

The preferred substrates used for the production of the lithographic printing plates using the photosensitive composition of the present invention include hydrophilized aluminum plates, anodized aluminum plates, grained aluminum plates and silicate electrodeposited aluminum plates. In addition, also usable are zinc plates, stainless steel plates, chrome treated steel plates and hydrophilized plastic films or paper.

The preferred examples of the substrates suitable for the production of proofs for printings, films for an overhead projector and films for the second drawings are transparent films such as a polyethylene terephthalate film or a triacetyl cellulose film or those obtained by subjecting the surface of the plastic film to chemical or physical mat-treatment. On the other hand, the preferred examples of the substrates suitable for the production of photomask films are polyethylene telephatalate films obtained by vapor-depositing them with aluminum, aluminum alloy or chrome and polyethylene telephatalate films provided thereon a coloring layer. In addition to the above exemplified substrates, a variety of substrates such as steel plates, copper-plated plates, glass plates and silicone wafers may be used for the production of photoresists. These photoresists are produced by coating the photosensitive composition on the above substrates.

The activating ray source usable in exposing the photosensitive composition of the present invention is preferably, for example, mercury lamp, metal halide lamp, xenon lamp, chemical lamp, carbon arc lamp g-rays stepper or i-rays stepper. Further, a scanning exposure method using a high-density energy beam (laser beam or electron rays) can also be employed in the present invention. The laser beam is preferably, helium/neon laser, argon laser, krypton ion laser, helium/cadmium laser or excimer laser.

The developer for the photosensitive composition of the present invention is preferably an aqueous solution of an alkali such as sodium silicate, potassium silicate, sodium hydroxide, potassium hydroxide, lithium hydroxide, sodium tertiary phosphate, disodium hydrogenphosphate, ammonium tertiary phosphate, diammonium hydrogenphosphate, sodium metasilicate, sodium hydrogencarbonate, sodium carbonate, aqueous ammonia or tetramethylammonium hydroxide. The amount of the developer is such that the concentration thereof is 0.1 to 10% by weight, preferably 0.2 to 5% by weight.

If necessary, a surfactant or an organic solvent such as an alcohol can be added to the aqueous alkaline solution.

The following Preparation Examples and Examples will further illustrate the present invention, which by no means limit the scope of the present invention.

PREPARATION EXAMPLE 1

Preparation of Exemplified Compound (1-3)

An aqueous solution of 34 parts by weight of sodium 9,10-dimethoxyanthracene-2-sulfonate in 500 parts by weight of water was gradually dropwise added under stirring to an aqueous solution of 36 parts by weight of diphenyliodonium perchlorate in 500 parts by weight of water. The mixture was stirred for 2 hr. to form the precipitate of the product. The product was filtered off and then washed with 200 parts of water. The salt thus formed was dried under reduced pressure at 40° C. to obtain diphenyliodonium·9,10-dimethoxyanthracene-2-sulfonate in a yield of 89.4%.

PREPARATION EXAMPLE 2

Preparation of Exemplified Compound (2-5)

An aqueous solution of 31 parts by weight of 2-hydroxy-4-methoxybenzophenone-5-sulfonic acid in 500 parts by weight of water was gradually dropwise added under stirring to an aqueous solution of 30 parts by weight of triphenylsulfonium chloride in 100 parts by weight of water. After the dropwise addition, the mixture was stirred for 2 hr. to form the precipitate of the product. The product was filtered off and then washed with 200 parts of water. The salt thus formed was dried under reduced pressure at 40° C. to obtain triphenylsulfonium ·2-hydroxy-4-methoxybenzophenone-5-sulfonate in a yield of 80.4%.

EXAMPLE 1

An aluminum sheet having a thickness of 0.24 mm was degreased by immersing it in a 10% aqueous solution of sodium tertiary phosphate maintained at 80° C. for 3 min. Then, the sheet was grained with a nylon brush, etched with sodium aluminate for about 10 seconds. and desmutted with a 3% aqueous solution of sodium hydrogensulfate. The aluminum sheet was subjected to anodic oxidation in a 20% sulfuric acid solution at a current density of 2 A/dm$^2$ for 2 min.

Five kinds of sensitive solutions [A]-1 to [A]-5 were prepared by varying the kind of the compound of the present invention. The sensitive solution was applied to the aluminum sheet treated by the anodic oxidation as described above and then dried at 100° C. for 2 min. to prepare the respective photosensitive lithographic printing plates [A]-1 to [A]-5. The amount of the solution applied was 1.4 g/m$^2$ on dry basis in all the cases.

The compounds of the present invention used for the preparation of the sensitive solutions [A]-1 to [A]-5 are shown in Table 1.

| Sensitive solution [A] | |
|---|---|
| The compound of the present invention shown in Table 1 | 0.47 g |
| Cresol/formaldehyde/novolak resin | 1.1 g |
| Oil blue #603 (a product of Orient Kagaku Kogyo Co., Ltd.) | 0.01 g |
| Ethylene dichloride | 10 g |
| Methyl cellosolve | 10 g |

Then, the following sensitive solution [B] was prepared for the comparative purpose and then applied to the aluminum sheet in the same manner as that of the sensitive solution [A] to prepare the photosensitive lithographic printing plate [B].

| Sensitive solution [B] | |
|---|---|
| Diphenyliodonium.hexafluorophosphate | 0.47 g |
| Cresol/formaldehyde/novolak resin | 1.1 g |
| Oil blue #603 (a product of Orient Kagaku Kogyo Co., Ltd.) | 0.01 g |
| Ethylene dichloride | 10 g |
| Methyl cellosolve | 10 g |

The amount of the solution applied was 1.4 g/m$^2$ on dry basis.

A gray scale having a density gradient of 0.15 was firmly attached to the photosensitive layer of each of the photosensitive lithographic printing plates [A] -1 to [A] -5 and [B] and exposed to light of a 30A. carbon arc lamp from a distance of 70 cm. The exposed photosensitive lithographic printing plates [A] -1 to [A] -5 and [B] were immersed in an aqueous 2.5 wt % sloution of potassium silicate (SiO$_2$/K$_2$O molar ratio=1.2) at 25° C. for 60 sec. to determine the exposure time at which the fifth stage of the gray scale having a density gradient of 0.15 becomes completely clear. The results are shown in Table 1.

TABLE 1

| Photosensitive lithographic printing plate | Compound of the present invention used | Exposure time (Sec.) |
|---|---|---|
| [A]-1 | (1-2) | 35 |
| [A]-2 | (1-3) | 20 |
| [A]-3 | (1-11) | 40 |
| [A]-4 | (2-4) | 35 |

TABLE 1-continued

| Photosensitive lithographic printing plate | Compound of the present invention used | Exposure time (Sec.) |
|---|---|---|
| [A]-5 | (2-21) | 40 |
| [B] | — | 70 |

As is apparent from Table 1, all of the photosensitive lithographic printing plates [A] -1 to [A] -5 using the compounds of the present invention had less exposure time and higher sensitivity than those of the photosensitive lithographic printing plate [B].

EXAMPLE 2

5 parts by weight of the compound of the present invention and 95 parts by weight of a novolak resin (a polymer obtained by condensing a 1:1 mixture of m-cresol and p-cresol with formalin under the existence of a sulfuric acid catalyst and having an average molecular weight of 3000) were dissolved in 300 parts by weight of methyl lactate to form a 25% by weight solution.

The three kinds of the compounds of the present invention used are shown in Table 2. Then, as the comparative example, the sensitive solution was prepared in the same manner as above except that diphenyliodonium ·tetrachloroborate was replaced for the compounds of the present invention.

The sensitive solution was spin-coated to a silicone wafer at 4000 rpm to form a coating film having a thickness of 1.0 μm on the wafer. Then, the film was pre-baked at 80° C., 10 min. and irradiated to light by using i-line stepper LD-5010 i (365 nm) (a product of Hitach,Ltd.). After the irradiation, the irradiated film was subjected to post-baking at 90° C., 10 min. and then immersed in a 2% by weight aqueous solution of tetramethylammonium hydroxide for 60 sec. to solubilize the irradiated portion. The "sensitivity" in Table 2 means the least energy at which images are obtainable without causing damage to the film in non-irradiated portions.

TABLE 2

| Micro-photoresist (No.) | Compound used | Sensitivity (mj/cm²) |
|---|---|---|
| 1 | Compound (1-2) of the present invention | 614 |
| 2 | Compound (1-3) of the present invention | 83 |
| 3 | Compound (2-4) of the present invention | 630 |
| Comparative Example | Diphenyliodonium tetrachloroborate | No image was obtained |

As is apparent from Tables 1 and 2, the photosensitive compositions using the compounds of the present invention were sensitive not only to carbon arc light rays (in Table 1) but also to i-rays stepper light rays (in Table 2).

As described above, it is clear that all of the photosensitive compositions using the compounds of the present invention has the higher sensitivity and the wider range area of the photosensitive wavelength area than those of the comparative example.

What is claimed is:

1. A positive working photosensitive composition comprising a polymeric compound insoluble in water but soluble in an aqueous alkaline solution and an aromatic sulfonic acid salt of an onium compound, wherein the aromatic sulfonic acid salt of the onium compound is at least one member selected from the group consisting of the compounds represented by the following general formula (1) or (2):

wherein:
Ar¹ and Ar² may be the same or different and each represents a substituted or unsubstituted aromatic group,
R¹, R² and R³ may be the same or different and each represents a substituted or unsubstituted alkyl group or a substituted or unsubstituted aromatic group, and
X represents an aromatic sulfonic acid anion derived from an acid selected from the group consisting of a condensed polycyclic aromatic sulfonic acid, an anthraquinonesulfonic acid, a phenanthraquinonesulfonic acid, a naphthoquinonesulfonic acid, a sulfonic acid group-containing dye and 2-hydroxy-4-methoxybenzophenone-5-sulfonic acid.

2. The composition of claim 1, wherein the aromatic sulfonic acid salt of the onium compound is the compound represented by the general formula (1).

3. The composition of claim 2, wherein Ar¹ and Ar² each represents an aromatic group substituted by an alkyl group, a haloalkyl group, a cycloalkyl group, an aryl group, an alkoxy group, a nitro group, an oxo group, an alkoxycarbonyl group, a hydroxy group, a mercapto group or a halogen atom.

4. The composition of claim 3, wherein Ar¹ and Ar² each represents an aromatic group substituted by an alkyl group having 1–8 carbon atoms, an alkoxy group having 1–8 carbon atoms, a nitro group or a chlorine atom.

5. The composition of claim 2, wherein X - represents an anion selected from the group consisting of naphthalene-1-sulfonic acid, naphthalene-2-sulfonic acid, anthracene-1-sulfonic acid, 9-nitroanthracene-1-sulfonic acid, 9,10-dichloroanthrace-2-sulfonic acid, 9,10-dimethoxyanthracene-2-sulfonic acid, 9,10-diethoxyanthracene-2-sulfonic acid, anthracene-2-sulfonic acid, phenanthrene-2-sulfonic acid, 9-bromophenanthrene-3-sulfonic acid, 1-methyl-7-isopropylphenanthrene-3-sulfonic acid, pyrene-2-sulfonic acid, benz[a]anthracene-4-sulfonic acid, triphenylene-2-sulfonic acid, chrysene-6-sulfonic acid, 5,6-dichloroanthracene-3-sulfonic acid, 6-nitroacenaphthene-5-sulfonic acid, 2-t-butylnaphthalene-7-sulfonic acid, 9,10-dioxo-9,10-dihydroanthracene-2-sulfonic acid, 1-bromo-9,10-dioxo-9,10-dihydroanthracene-2-sulfonic acid, 2-chloro-9,10-dioxo-9,10-dihydroanthracene-2-sulfonic acid, 9,10-dioxo-9,10-dihydrophenanthrene-3-sulfonic acid, 1,2-naphthoquinone-4-sulfonic acid, 1,2-naphthoquinonediazide-4-sulfonic acid, 1,2-naphthoquinonediazide-5-sulfonic acid, and 2-hydroxy-4-methoxybenzophenone-5-sulfonic acid.

6. The composition of claim 2, wherein the aromatic sulfonic acid salt of the onium compound is at lease one memeber selected from the compounds represented by the following formulas:
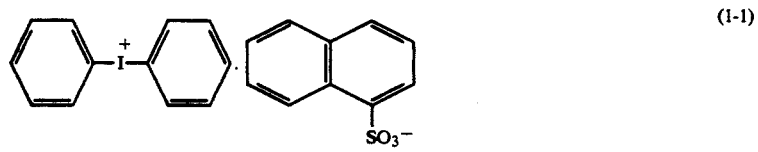
(1-1)
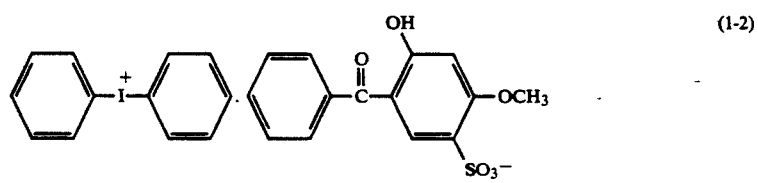
(1-2)
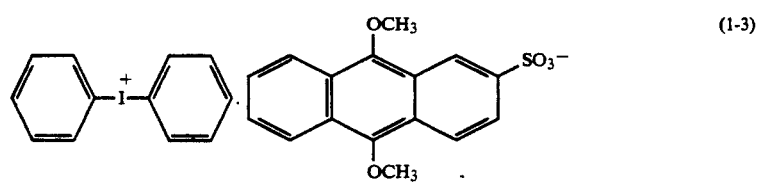
(1-3)
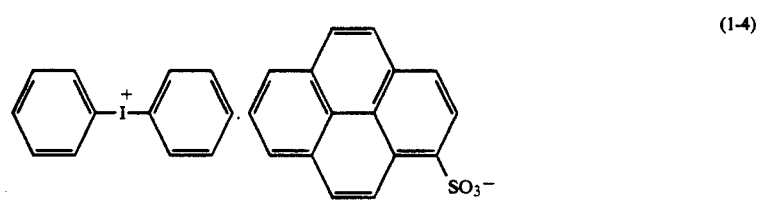
(1-4)
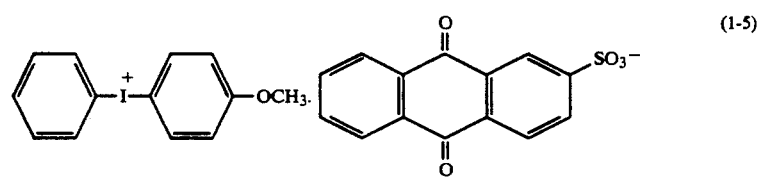
(1-5)
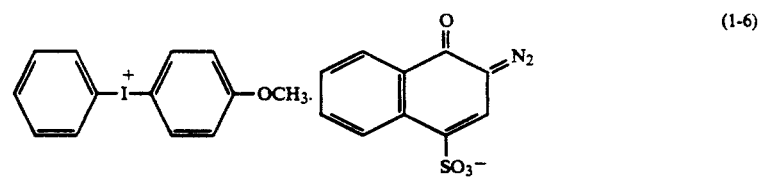
(1-6)
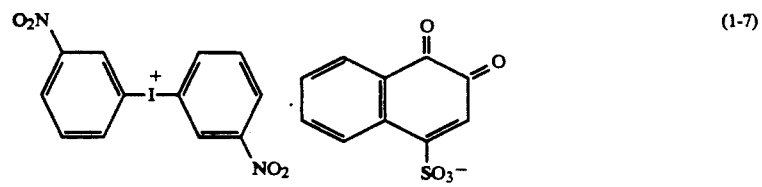
(1-7)
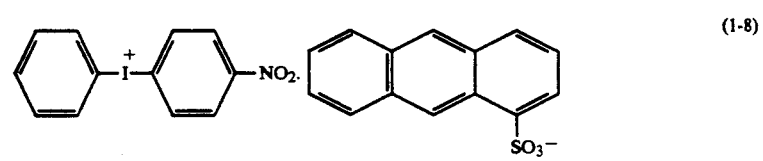
(1-8)

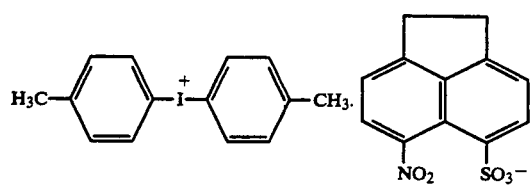
(1-9)
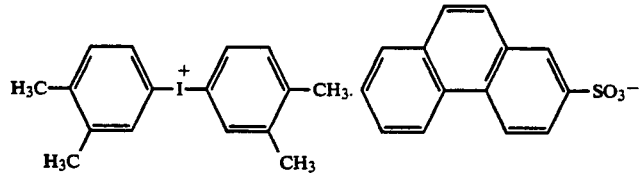
(1-10)
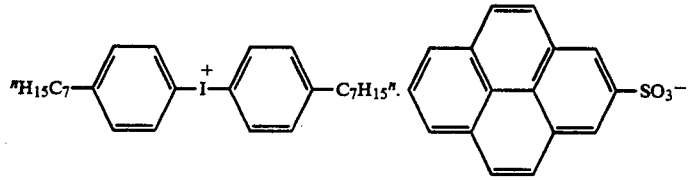
(1-11)
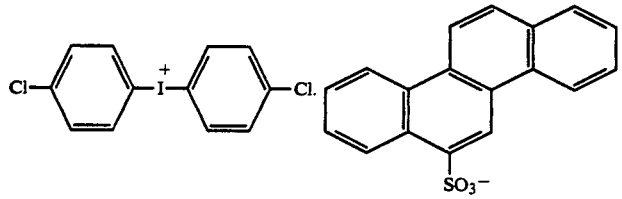
(1-12)
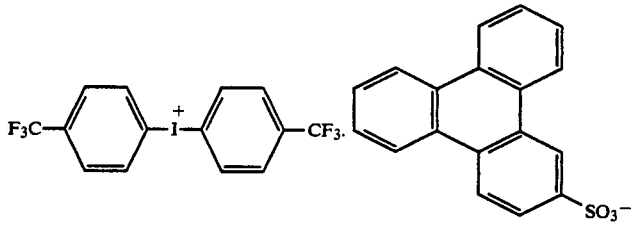
(1-13)
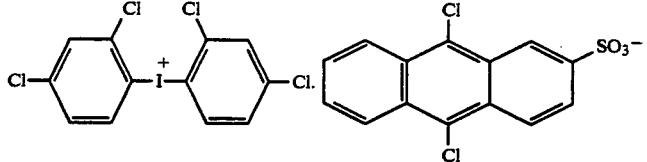
(1-14)
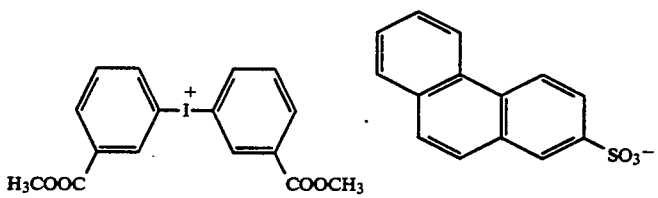
(1-15)
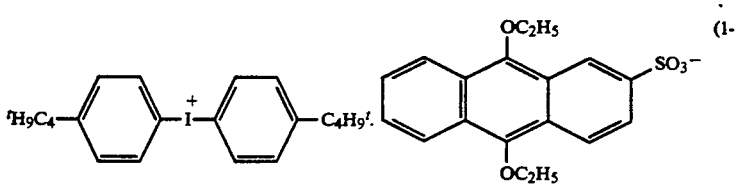
(1-16)

-continued

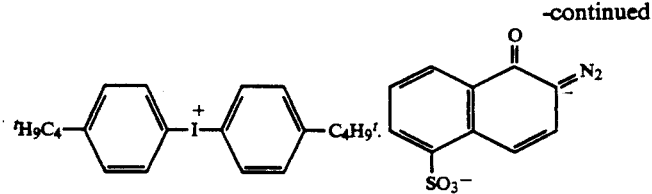
(1-17)

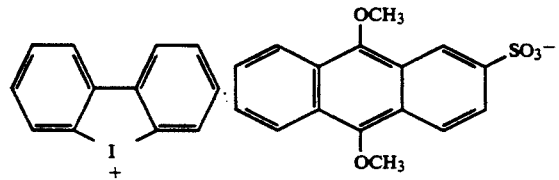
(1-18)

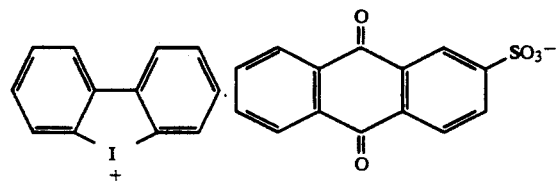
(1-19)

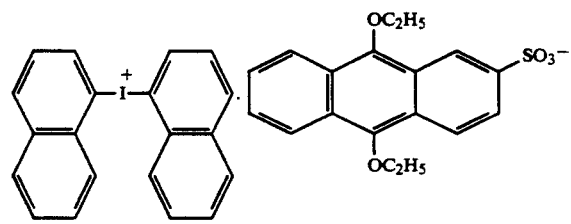
(1-20)

7. The composition of claim 1, wherein the aromatic sulfonic acid salt of the onium compound is the compound represented by the general formula (2).

8. The composition of claim 7, wherein said $R^1$, $R^2$ and $R^3$ each represents an aryl group having 6–14 carbon atoms, an alkyl group having 1–8 carbon atoms or a substituted derivative thereof.

9. The composition of claim 8, wherein said $R^1$, $R^2$ and $R^3$ each represents an aryl group substituted by an alkoxy group having 1–8 carbon atoms, an alkyl group having 1–8 carbon atoms, a nitro group, a carbonyl group, a hydroxy group, a halogen atom, or an alkyl group substituted by an alkoxy group having 1–8 carbon atoms, an oxo group or an alkoxycarbonyl group.

10. The composition of claim 7, wherein $X^-$ represents an anion selected from the group consisting of naphthalene-1-sulfonic acid, naphthalene-2-sulfonic acid, anthracene-1-sulfonic acid, 9-nitroanthracene-1-sulfonic acid, 9,10-dichloroanthrace-2-sulfonic acid, 9,10-dimethoxyanthracene-2-sulfonic acid, 9,10-diethoxyanthracene-2-sulfonic acid, anthracene-2-sulfonic acid, phenanthrene-2-sulfonic acid, 9-bromophenanthrene-3-sulfonic acid, 1-methyl-7-isopropylphenanthrene-3-sulfonic acid, pyrene-2-sulfonic acid, benz[a]anthracene-4-sulfonic acid, triphenylene-2-sulfonic acid, chrysene-6-sulfonic acid, 5,6-dichloroanthracene-3-sulfonic acid, 6-nitroacenaphthene-5-sulfonic acid, 2-t-butylnaphthalene-7-sulfonic acid, 9,10-dioxo-9,10-dihydroanthracene-2-sulfonic acid, 1-bromo-9,10-dioxo-9,10-dihydroanthracene-2-sulfonic acid, 2-chloro-9,10-dioxo-9,10-dihydroanthracene-2-sulfonic acid, 9,10-dioxo-9,10-dihydrophenanthrene-3-sulfonic acid, 1,2-naphthoquinone-4-sulfonic acid, 1,2-naphthoquinonediazide-4-sulfonic acid, 1,2-naphthoquinonediazide-5-sulfonic acid, and 2-hydroxy-4-methoxybenzophenone-5-sulfonic acid.

11. The composition of claim 7, wherein the aromatic sulfonic acid salt of the onium compound is at leaset one memeber selected from the compounds represented by the following formulas:

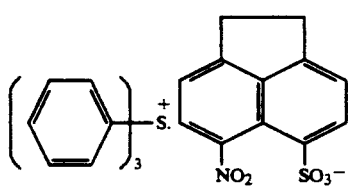
(2-1)

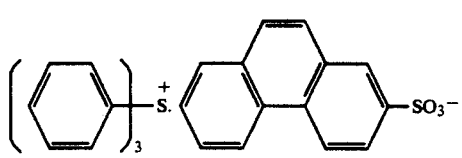
(2-2)

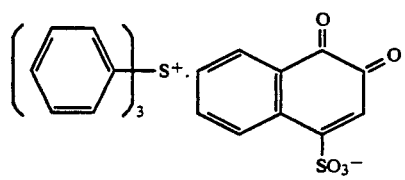 (2-3)
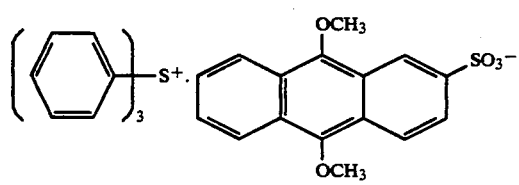 (2-4)
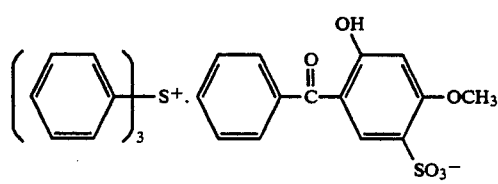 (2-5)
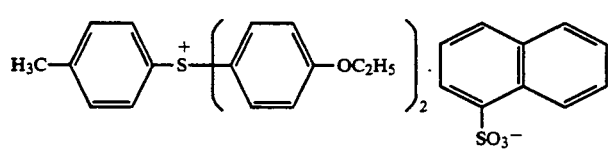 (2-6)
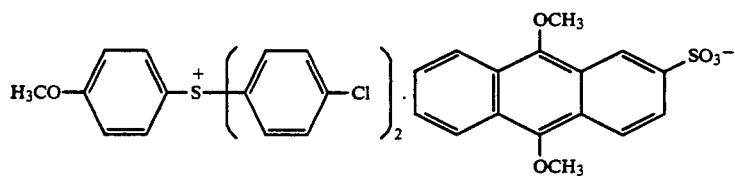 (2-7)
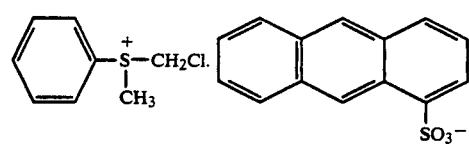 (2-8)
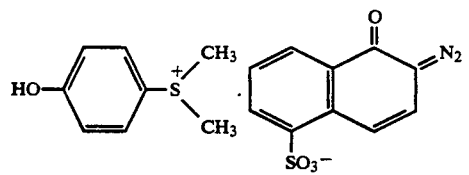 (2-9)
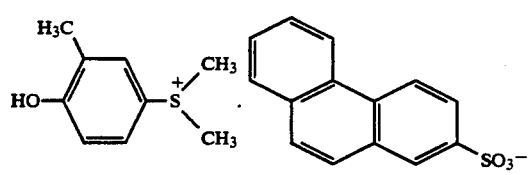 (2-10)
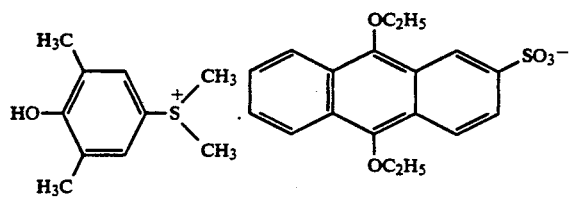 (2-11)

-continued
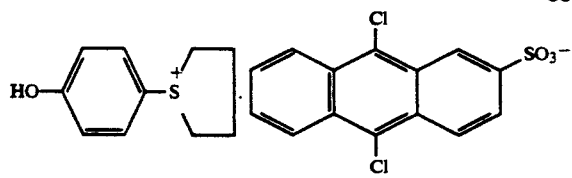 (2-12)
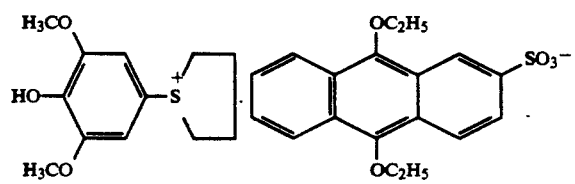 (2-13)
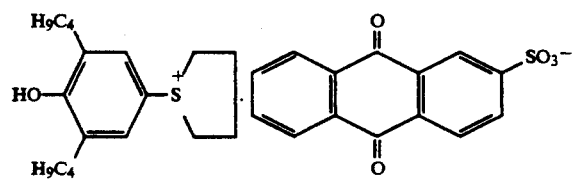 (2-14)
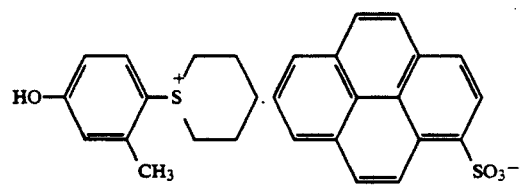 (2-15)
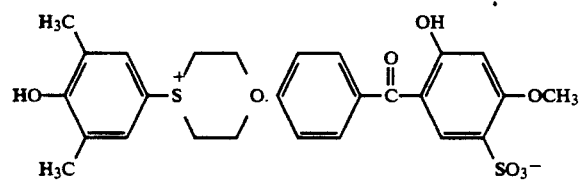 (2-16)
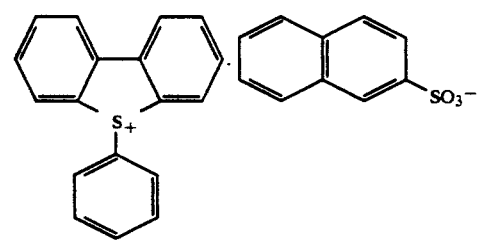 (2-17)
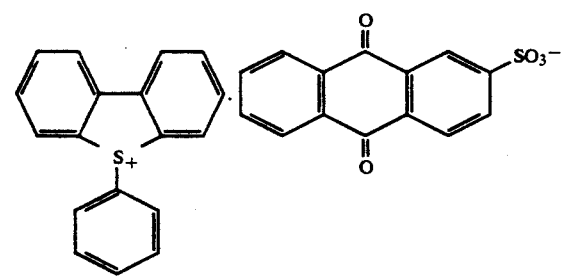 (2-18)
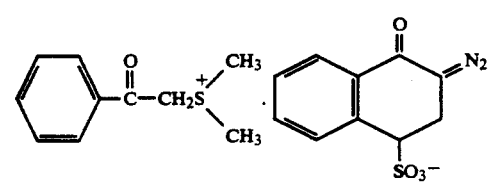 (2-19)

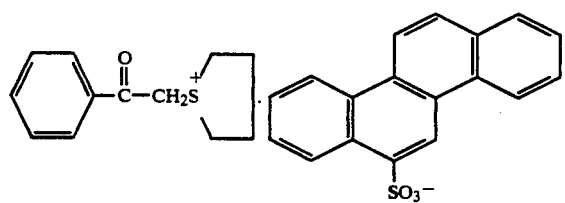 (2-20)
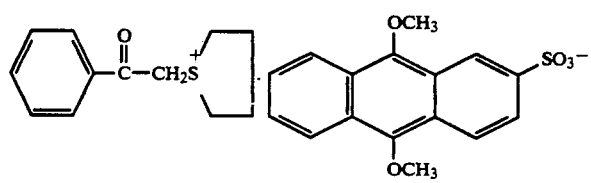 (2-21)
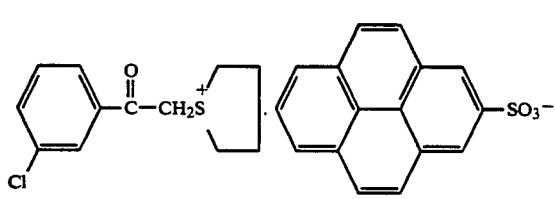 (2-22)
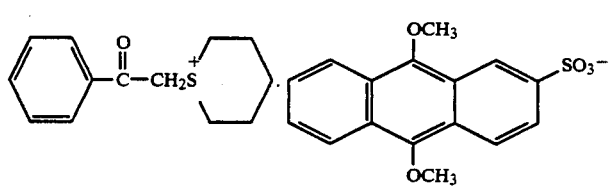 (2-23)
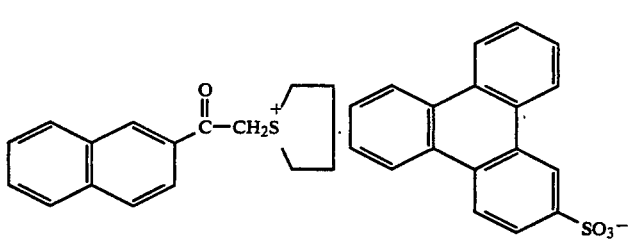 (2-24)
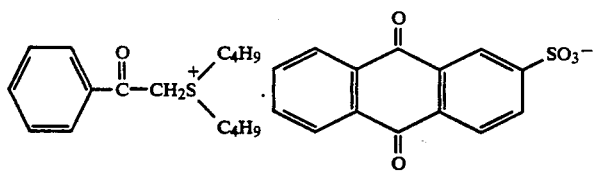 (2-25)
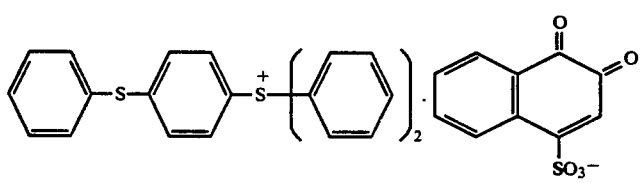 (2-26)
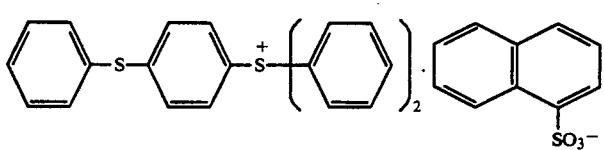 (2-27)

-continued

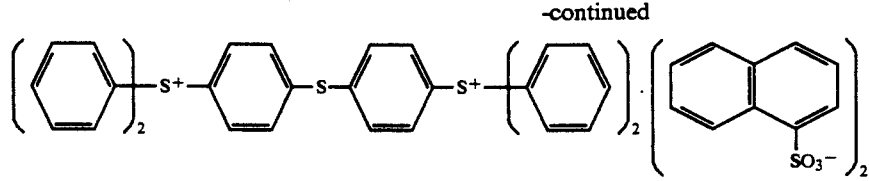

(2-28)

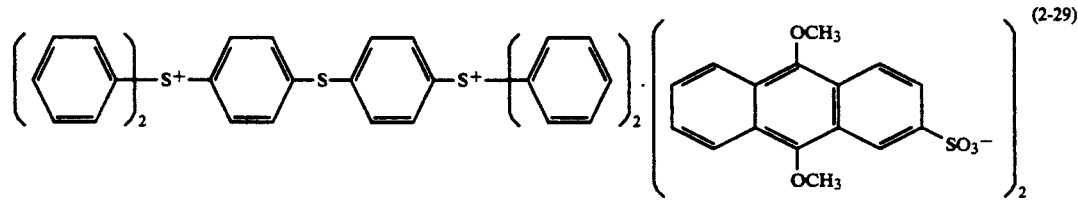

(2-29)

12. The composition of claim 1, wherein the amount of the aromatic sulfonic acid salt of the onium compound is 2–60% by weight based on the total weight of the photosensitive composition.

13. The composition of claim 12, wherein the amount of the aromatic sulfonic acid salt of the onium compound is 5–40% by weight based on the total weight of the photosensitive composition.

14. The composition of claim 1, wherein the polymeric compound is a novolak phenolic resin.

15. The composition of claim 14, wherein the polymeric compound is one member selected from the group consisting of a condensate of formaldehyde with a phenol derivative, polyvinylphenol, a hydroxyphenylmethacrylamide copolymer and a sunfonamide group-containing polymeric compound.

16. The composition of claim 1, the amount of the polymeric compound is 20–95% by weight based on the total weight of the photosensitive composition.

17. The composition of claim 16, the amount of the polymeric compound is 50–85% by weight based on the total weight of the photosensitive composition.

* * * * *